United States Patent
Weiss (10) Patent No.: US 9,949,875 B1
(45) Date of Patent: Apr. 24, 2018

(54) RETINAL AND OPTIC NERVE AUTOLOGOUS BONE-MARROW DERIVED STEM CELL SURGERY

(71) Applicant: Jeffrey N. Weiss, Parkland, FL (US)

(72) Inventor: Jeffrey N. Weiss, Parkland, FL (US)

( * ) Notice: Subject to any disclaimer, the term of this patent is extended or adjusted under 35 U.S.C. 154(b) by 0 days.

(21) Appl. No.: 14/825,887

(22) Filed: Aug. 13, 2015

Related U.S. Application Data (63) Continuation of application No. 14/794,533, filed on Jul. 8, 2015.

(60) Provisional application No. 62/021,797, filed on Jul. 8, 2014.

(51) Int. Cl.
*A61F 9/00* (2006.01)
*A61F 9/007* (2006.01)
*A61M 5/32* (2006.01)

(52) U.S. Cl.
CPC .......... *A61F 9/00736* (2013.01); *A61F 9/007* (2013.01); *A61F 9/0008* (2013.01); *A61F 9/0017* (2013.01); *A61M 5/3286* (2013.01); *A61M 2202/0021* (2013.01); *A61M 2202/10* (2013.01); *A61M 2205/02* (2013.01); *A61M 2210/0612* (2013.01)

(58) Field of Classification Search
CPC .. A61F 9/00736; A61F 9/0017; A61F 9/0008; A61F 9/007; A61M 5/3286; A61M 2202/0021; A61M 2210/0612; A61M 2202/10; A61M 2205/02
See application file for complete search history.

(56) References Cited

U.S. PATENT DOCUMENTS

| | | | |
|---|---|---|---|
| 2003/0059755 A1* | 3/2003 | D'Amico | A61B 17/3417 434/272 |
| 2003/0208181 A1* | 11/2003 | Geise | A61M 1/0218 604/406 |
| 2004/0039401 A1* | 2/2004 | Chow | A61F 9/007 606/129 |
| 2005/0080375 A1* | 4/2005 | Kadziauskas | A61F 9/0008 604/39 |
| 2007/0191863 A1* | 8/2007 | De Juan, Jr. | A61F 9/0017 606/108 |
| 2009/0264813 A1* | 10/2009 | Chang | A61F 9/0017 604/60 |
| 2010/0211079 A1* | 8/2010 | Aramant | A61F 9/0017 606/107 |
| 2012/0129676 A1* | 5/2012 | Duffy | A61B 10/025 494/37 |
| 2013/0189230 A1* | 7/2013 | Shoichet | A61K 9/0024 424/93.7 |
| 2013/0296825 A1* | 11/2013 | Lerner | A61M 5/3145 604/506 |

(Continued)

FOREIGN PATENT DOCUMENTS

WO WO 2013154336 A1 * 10/2013 ........... A61F 9/0017

*Primary Examiner* — Emily Schmidt
*Assistant Examiner* — Amber Stiles
(74) *Attorney, Agent, or Firm* — Daniel S. Polley, P.A.

(57) ABSTRACT

A novel retinal and optic nerve autologous bone-marrow derived stem cell surgery method is provided. The method generally includes the separation of stem cells from the bone-marrow of a patient, and the reintroduction of the cells to treat various optic nerve and retinal conditions of the eye. Novel needle embodiments which can be used during the stem cell surgery are also described.

21 Claims, 7 Drawing Sheets

(56) References Cited

U.S. PATENT DOCUMENTS

2015/0112282 A1* 4/2015 Jung, II ................ A61F 9/0017
                                                            604/272

* cited by examiner

RETINAL AND OPTIC NERVE AUTOLOGOUS BONE-MARROW DERIVED STEM CELL SURGERY

This application is a continuation of U.S. application Ser. No. 14/794,533, filed Jul. 8, 2015, which application claims the benefit of and priority to U.S. Provisional Patent Application Ser. No. 62/021,797, filed Jul. 8, 2014, all of the above-identified applications are incorporated by reference in their entireties for all purposes.

1. FIELD OF THE DISCLOSURE

The present disclosure relates to the use of cell-based therapies in the treatment of medical conditions.

2. BACKGROUND

A stem cell is a cell that can reproduce and has the potential to change or differentiate into another type of cell. At the present time, there are 4 basic types of stem cells:
1. Embryonic Cells are generally taken from very early fertilized embryos. They can give rise to any type of cell, but unrestrained with respect to differentiation, may result in tumor formation.
2. Parthenogenetic Cells are taken from unfertilized eggs. Since the eggs are not fertilized the stem cells they produce are genetically compatible with the woman who donated the egg.
3. "Adult" Stem Cells are found in different organs, including bone marrow, adipose tissue, umbilical cord blood and fetal tissue. Like embryonic stem cells, adult stem cells can reproduce, but less so than embryonic, and unlike embryonic cells, adult stem cells generally form cells in their own tissue type, making the chance of tumor formation much less likely.
4. Induced Pluripotent Stem Cells are differentiated cells that can be stimulated to return to an undifferentiated state.

There are many conditions of the optic nerve and of the retina of the eye that result in blindness for which there is no effective treatment to restore or in many cases, to prevent the loss of vision.

SUMMARY OF THE DISCLOSURE

The present disclosure describes the novel use of cell-based therapies in the treatment of optic nerve and retinal conditions of the eye, including, without limitation, treating previously untreatable optic nerve and retinal conditions. Novel needles for use in cell-based therapy treatments, as well as for other eye-related conditions, are also described.

DETAILED DESCRIPTION

In connection with the disclosure, the following definitions will be used.
1. Retrobulbar Injection—The cells are injected behind the eye into the posterior orbit or eye socket and tissues surrounding the eye.
2. Subtenons—The cells are injected under one of the layers of tissue overlying the white part, or sclera, of the eye. The injection is done from the front of the eye and the material spreads under the Tenons tissue posteriorly, towards the back of the eye.
3. Intravitreal—The cells are injected into the vitreous cavity of the eye.
4. Vitrectomy—In this procedure, small instruments are placed into the eye and the vitreous body, (the natural gel inside the eye) is removed and replaced with a clear liquid. The surgeon then has access to inject cells into or under the retina or into a retinal blood vessel, into the optic nerve, or into the vitreous cavity.
5. Autologous—Derived or transferred from the same individual's body. Also known as an "autograft" or "autotransplant."

The disclosure described novel methods of treating previously untreatable optic nerve and retinal conditions.

Though not considered limiting, patients having one or more of the following conditions may benefit through one or more of the described novel cell based therapy treatments:

Retinal Conditions
1. Age-related Macular Degeneration
2. Cone Dystrophy
3. Cone-Rod Dystrophy
4. Retinitis Pigmentosa (Rod-Cone Dystrophies)

5. Stargardt's Macular Dystrophy
6. Myopic Degeneration
7. Status post Retinal Detachment repair with visual loss
8. Ischemic Retinopathies
9. Birdshot Retinopathy
10. Radiation Retinopathy
11. Presumed Ocular Histoplasmosis Syndrome
12. Autoimmune Retinopathy Optic Nerve Conditions
1. Anterior Ischemic Optic Neuropathy
2. Optic Nerve Trauma
3. Glaucoma
4. Optic Atrophy
5. Neuromyelitis Optica
6. Leber Hereditary Optic Neuropathy
7. Optic Nerve Hypoplasia
8. Autoimmune Optic Neuropathy
9. Dominant Optic Atrophy
10. Hereditary Optic Atrophy Novel stem-cell treatments described herein for the retinal conditions can include, without limitation:
1. Retrobulbar Injection
2. Subtenon Injection
3. Injection of stem cells into the vitreous cavity (with or without vitrectomy)
4. Vitrectomy with injection of stem cells under the retina
5. Vitrectomy with injection of stem cells into a retinal blood vessel Novel stem-cell treatments described herein for the optic nerve conditions can include, without limitation:
1. Retrolbulbar Injection
2. Subtenon Injection
3. Injection of stem cells into the vitreous cavity (with or without vitrectomy)
4. Vitrectomy with injection of stem cells into the optic nerve
5. Vitrectomy with injection of stem cells under the retina.

In connection with at least one of the treatments, approximately 3 cc of cells can be injected in the retrobulbar space, approximately 1 cc in the subtenon space, approximately 0.05 cc into the vitreous cavity (if a vitrectomy is not done), and if a vitrectomy is performed: approximately 0.3 cc into the vitreous cavity, approximately 0.3 cc into the subretinal space, approximately 0.1 cc into the retinal blood vessel, and/or, approximately 0.3 cc into the optic nerve. The remaining cells may be given to the patient intravenously.

It has been experimentally determined that the injection of approximately 0.5 cc or more of cells into the vitreous cavity of the vitrectomized eye may increase the risk of retinal detachment.

The retinal and subretinal environment can influence the differentiation and functionality of transplanted cells. Transplanted cells and the solution in which they reside, can secrete numerous molecules that may exert a beneficial effect on the eye even if they do not cure the underlying disease.

Novel Stem-Cell Treatment Procedures

Figure 1:
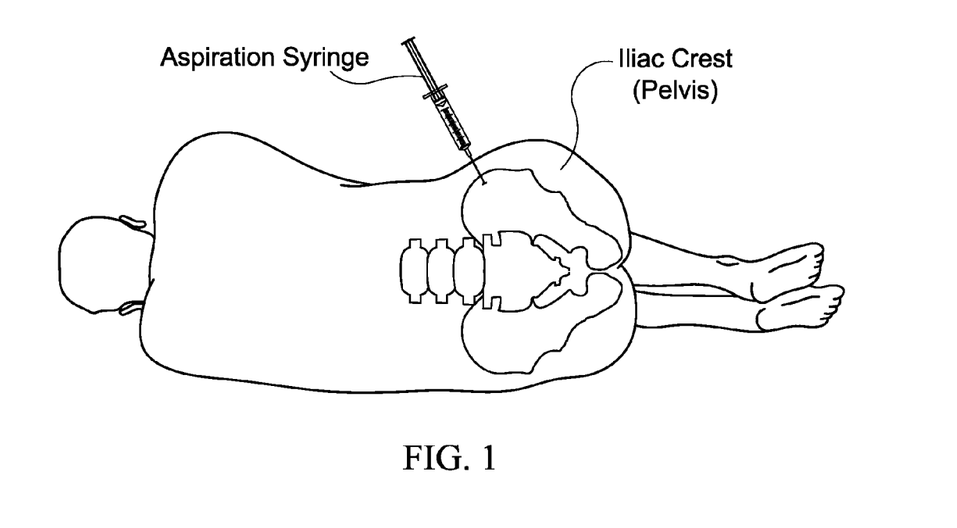
FIG. 1 illustrates the aspiration of bone-marrow from a patient's iliac crest step as part of at least one of the novel cell based therapy treatments of the present disclosure.
Figure 2:
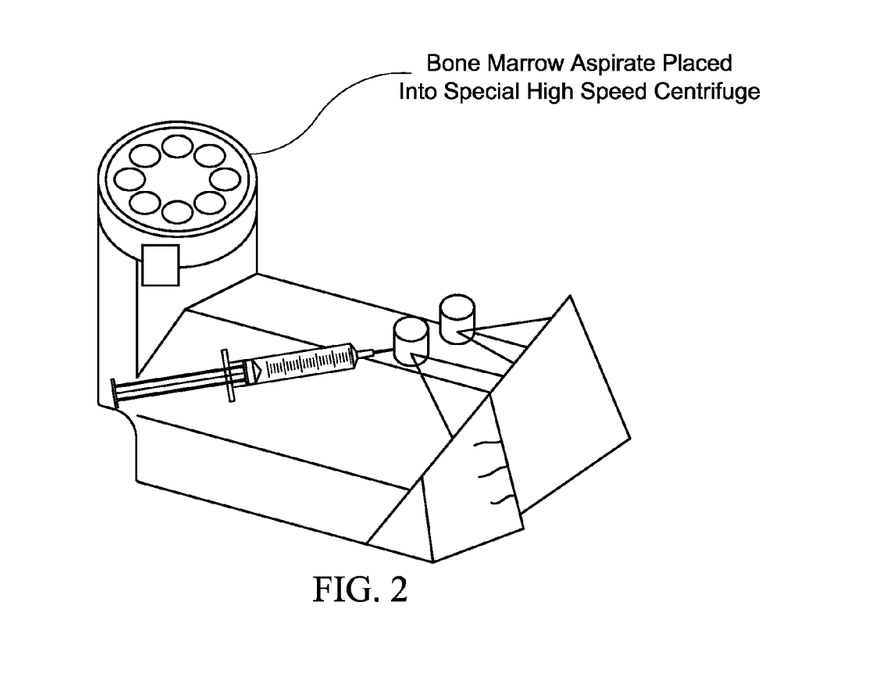
FIG. 2 illustrates the placement of bone-marrow aspirate in a special high-speed centrifuge to separate the stem cells from the remainder of the bone-marrow aspirate step as part of at least one of the novel cell based therapy treatments of the present disclosure.
Figure 3:
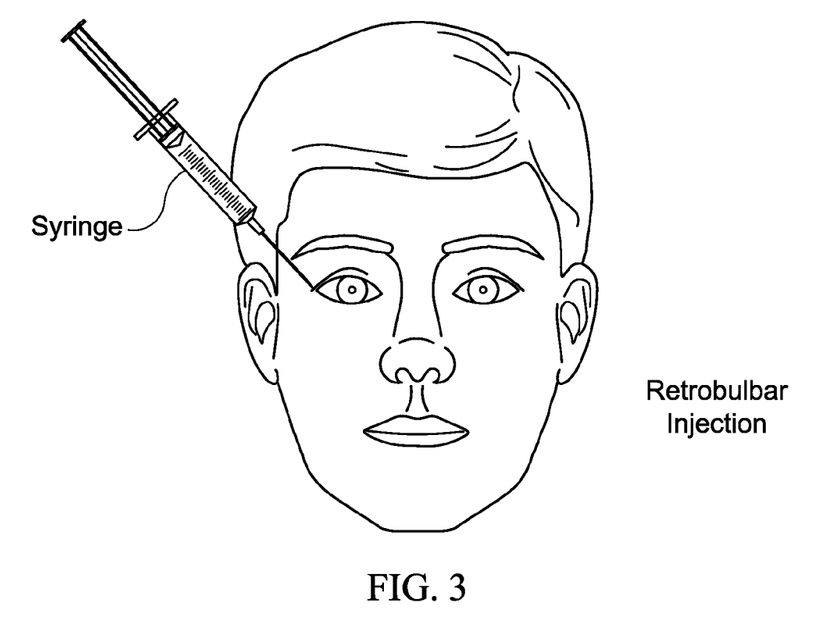
FIG. 3 illustrates the retrobulbar injection of stem cells step as part of at least one of the novel cell based therapy treatments of the present disclosure.
Figure 4:
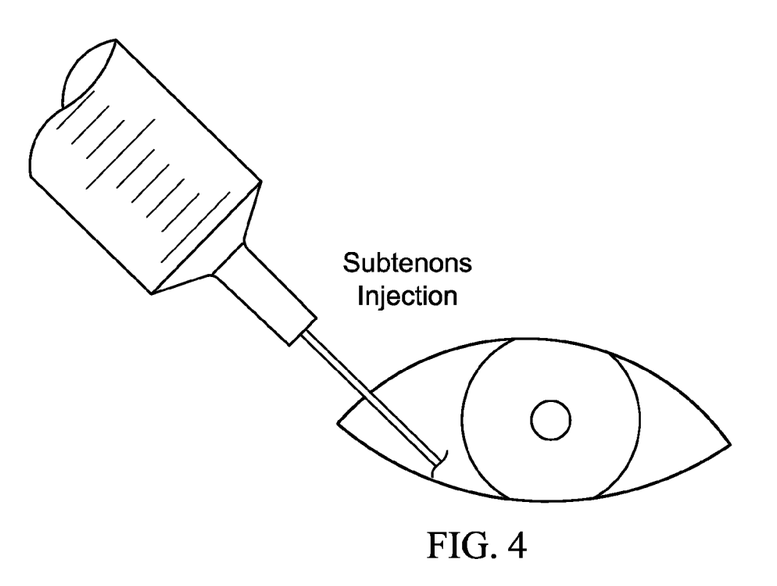
FIG. 4 illustrates the subtenons injection of stem cells step as part of at least one of the novel cell based therapy treatments of the present disclosure.
Figures 5, 6:
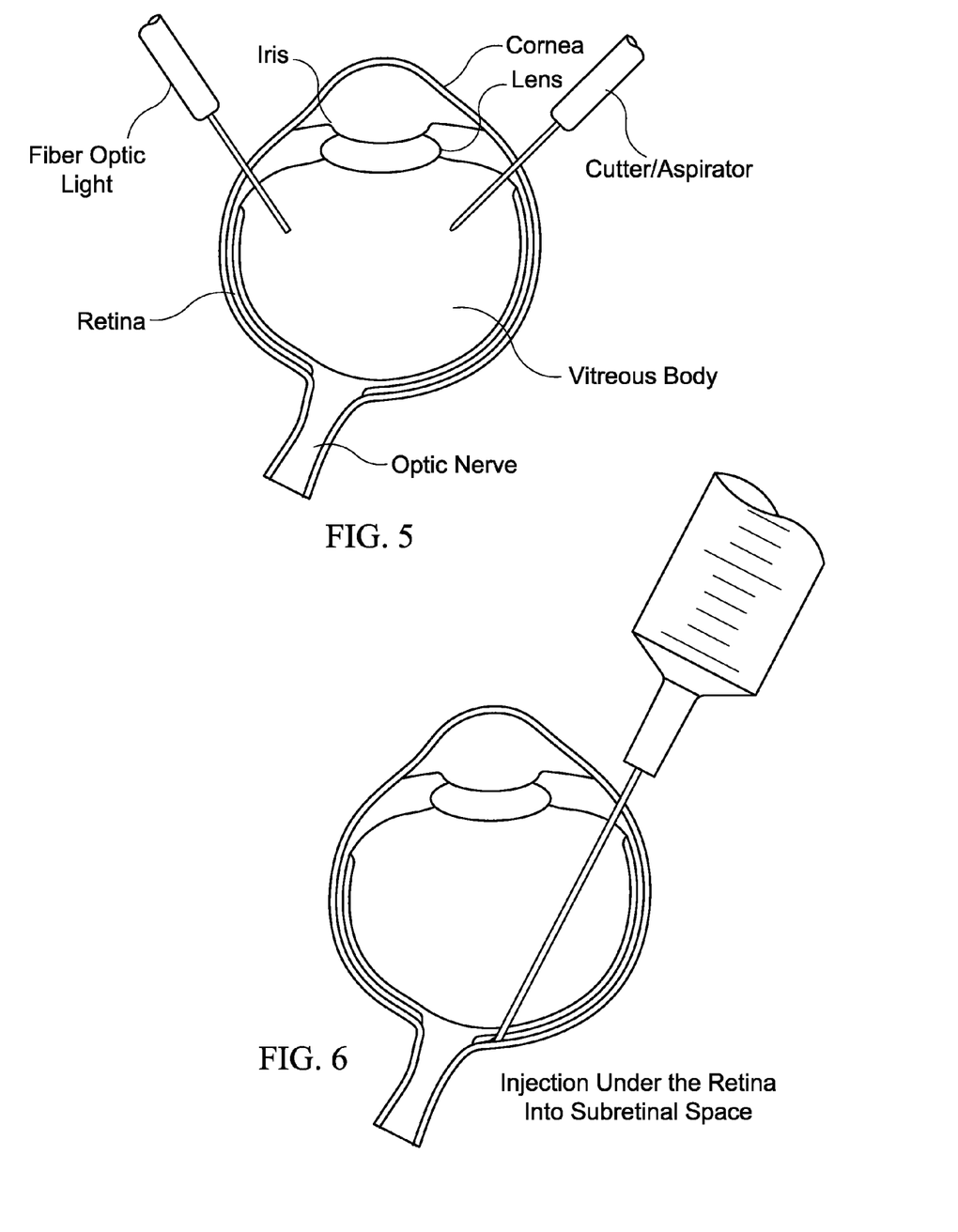
FIG. 5 illustrates the vitrectomy step as part of at least one of the novel cell based therapy treatments of the present disclosure.
FIG. 6 illustrates, preferably following a vitrectomy, the injection of the stem cells into the subretinal space step of at least one of the novel cell based therapy treatments of the present disclosure.
Figures 7, 8:
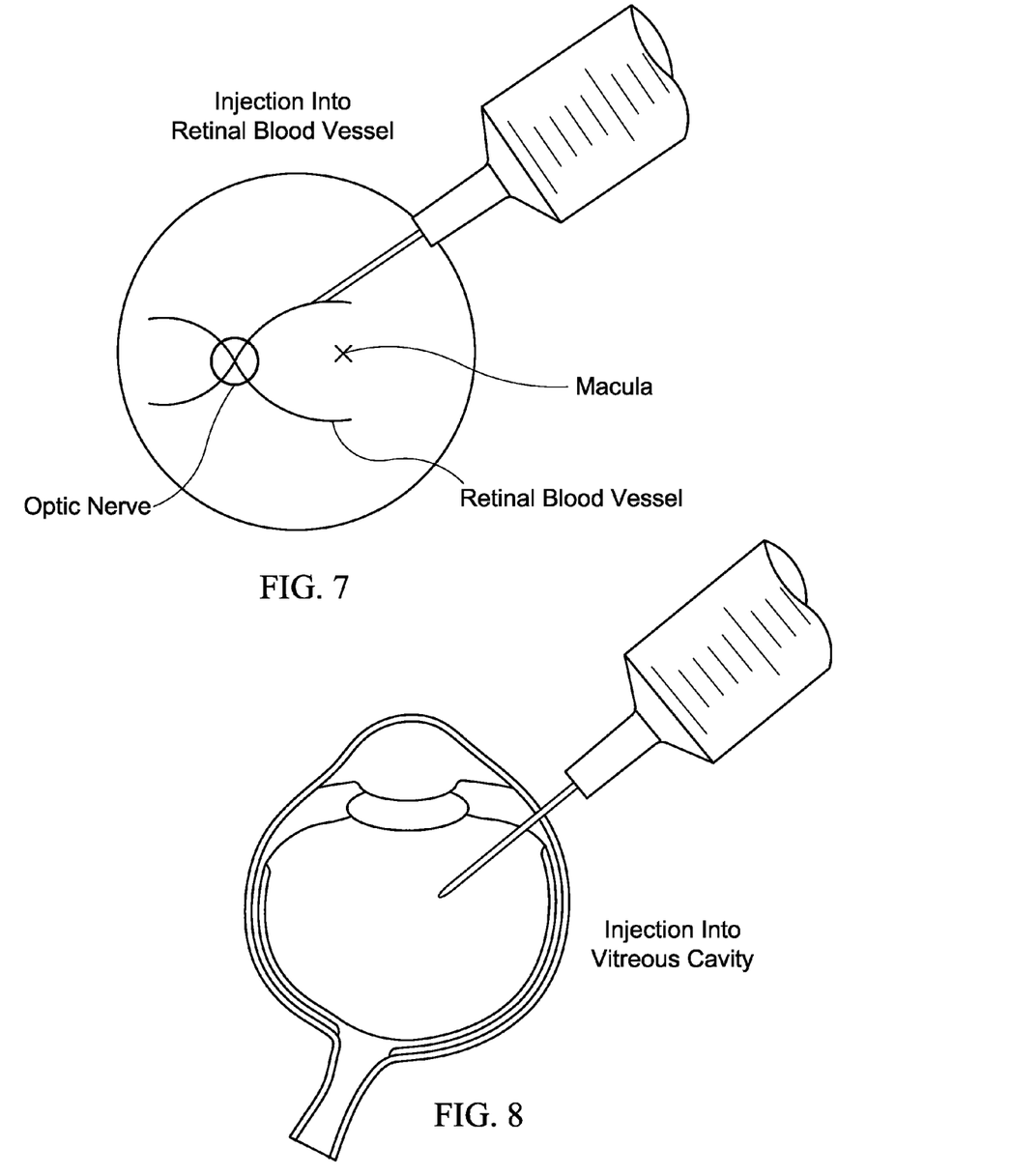
FIG. 7 illustrates the injection of the stem cells into the retinal blood vessel step of at least one of the novel cell based therapy treatments of the present disclosure.
FIG. 8 illustrates the injection of the stem cells into the vitreous cavity step of at least one of the novel cell based therapy treatments of the present disclosure, with or without vitrectomy.
Figure 9:
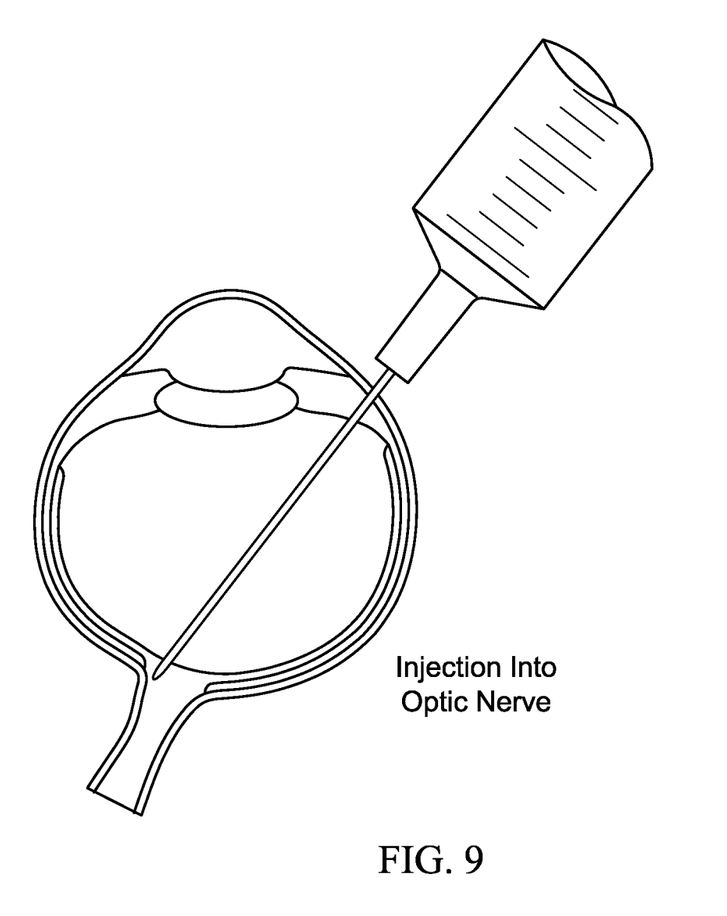
FIG. 9 illustrates, preferably following vitrectomy, the injection of the stem cells into the optic nerve step of at least one of the novel cell based therapy treatments of the present disclosure.

The patient can be placed under general anesthesia or given a local anesthetic. Under sterile conditions, the physician performs a bone marrow aspiration preferably from the patient's iliac crest (See FIG. 1) preferably using an aspiration syringe. A second bone marrow aspiration may be performed from the patient's opposite iliac crest in order to improve the cellular yield. The stem cells are preferably separated in a special high-speed centrifuge (See FIG. 2). As non-limiting examples, a machine manufactured by Harvest (Harvest Technologies Corp., Plymouth, Mass.) or an Angel machine (Arthrex, Inc., Naples, Fla.) is suitable. Typically, approximately 140 cc of bone marrow aspirate are placed into the machine that results in approximately 11 cc of nucleated cells of which approximately 10% may be stem cells. A protocol designed to minimize the presence of blood is used. Sodium citrate is used to prevent blood clotting. Sodium citrate provides a theoretical advantage over heparin in aiding the adherence of the stem cells.

The processing steps can include, without limitation:
1. Place sample into disposable container into the centrifuge chamber. Use appropriate counterbalance when processing one sample. Close centrifuge lid and press start.
2. Reduction of the volume of the red blood cells is accomplished by aligning the separation to the predetermined red blood cell level using the chamber port for optimal results.
3. If using a syringe with spacer, withdraw the plasma through the port until air bubbles are present.
4. If using a syringe without a spacer, re-suspend the bone marrow into the remaining plasma. Gently inject and mix together at least twice.
5. Transfer the sample back to the sterile field using transfer syringe on sterile field.

The remaining platelet rich plasma and nucleated cells are administered as discussed below depending on the patient's ocular and medical condition.

Non-Limiting Examples:

If the patient has had prior retinal surgery, including the placement of silicon oil into the eye, then the cells may be injected subtenons, retrobulbar and intravenous.

If the patient has risk factors for the performance of a vitrectomy, such as, but not limited to, uniocular status, high myopia, etc., then the cells may be injected intravitreally, subtenons, retrobulbar and intravenous.

If the patient is considered relatively low risk to undergo a vitrectomy then, as a non-limiting example, if the patient has a macular disease, such as age-related macular degeneration, a vitrectomy may be performed and the cells may be injected under the macular area. An example follows:

Preferred Procedure

Figure 12:
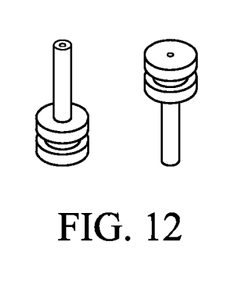
FIG. 12 is a perspective view of a cannula that can be used in connection with one or more of the disclosed novel cell based therapy treatments.

At the present time a port or cannula system can be used. The cannulas are placed through the sclera of the eye, typically in a manner to allow a shelved, self-sealing incision upon its removal from the eye. The cannula allows the various instruments to enter the eye through their insertion through the cannula, including the novel needles described below. For example, a 23 cannula will allow 23 gauge or smaller gauge instruments to enter the eye, a 25 gauge cannula will allow 25 gauge instruments, or smaller to enter the eye, and a 27 gauge will allow 27 gauge instruments, or smaller to enter the eye. A non-limiting example of a cannula that can be used in connection with the preferred procedures/treatments is shown in FIG. 12.

Though not considered limiting, three cannulas are placed into the sclera of the eye, at set-predetermined distances from the limbus of the eye in order not to cause a tear in the retina within the eye, and not to damage the internal lens of the eye. In a phakic individual, the cannulas are typically placed approximately 3.5 mm from the limbus of the eye.

One cannula is connected to an infusion line which allows the intraocular pressure to be maintained while the vitrectomy cutter removes material from the eye, the other 2 cannulas are generally used for the active instruments, such as a cutter, a fiber optic light pipe, forceps, scissors, pics, etc. which are designed to fit through the different gauge and appropriate sized cannulas.

Preferably, a core vitrectomy is initially performed. The cutter is replaced with a first novel subretinal needle described below that has been designed in order to make the procedure as safe as possible.

The first novel needle (FIGS. 10A and 10B) can be made of stainless steel, though other materials may be used, preferably fits through a standard 23 gauge cannula system into the eye. The needle can include an elongated portion having a tip portion. The tip portion of the needle is angled to approximately 135 degrees with respect to the elongated portion and tapers to 38 gauge at the tip end, and is sharp at the tip end. The needle retains the stiffness and sharpness at the tip portion of the needle to perforate the retina while making a self-sealing retinal hole. The needle can be connected via tubing to a syringe containing the stem cell or bone marrow fraction material.

Figure 10A:
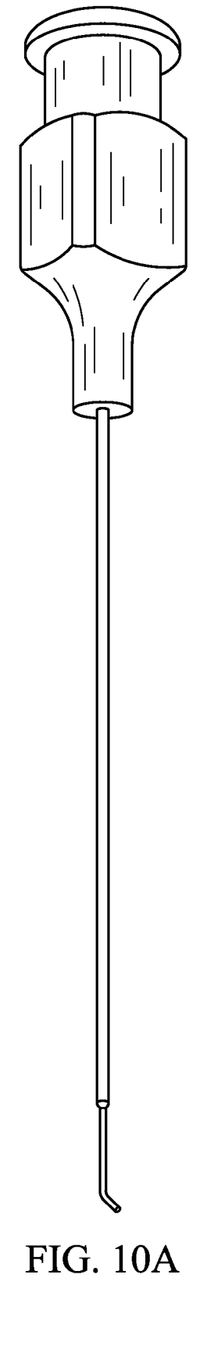
FIG. 10A is a perspective view of a novel needle for use with one or more of the disclosed novel cell based therapy treatments and other eye related procedures, including, without limitation, subretinal injections.
Figure 10B:
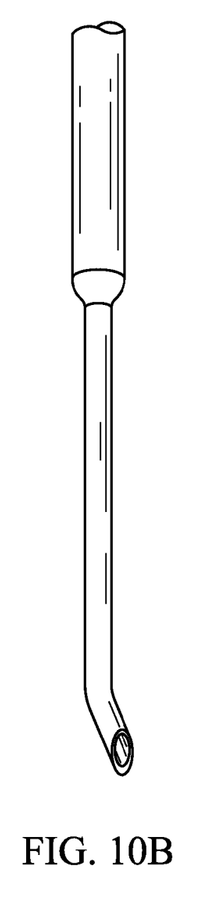
FIG. 10B is a perspective view of the tip end of the needle of FIG. 10A.

In the case of dry, or the geographic atrophy type of age-related macular degeneration, the tip of the first special needle is inserted through the retina at the margins of the atrophic area and the stem cell material, or bone marrow fraction, is injected into the atrophic area, under the retina.

Following injection, the first novel needle is removed in the same plane as it was placed, making a self-sealing retinal hole. Since the retinal hole is self-sealing, no laser photocoagulation, cryopexy, gas injection or other method of sealing the hole is required. A smaller dimension needle may also be employed and various materials to manufacture the needle may be used. The needle preferably retains the stiffness and sharpness at the tip of the needle to perforate the retina while making a self-sealing hole.

Figure 11A:
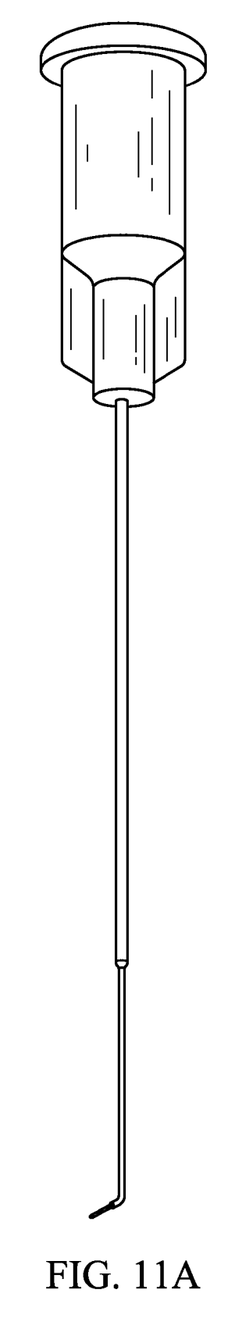
FIG. 11A is a perspective view of a second novel needle for use with one or more of the disclosed novel cell based therapy treatments and other eye related procedures, including without limitation, cannulations and injections.
Figure 11B:
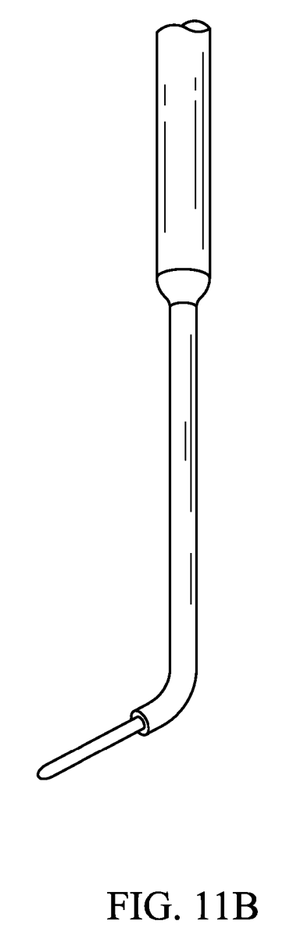
FIG. 11B is a perspective view of the tip end of the needle of FIG. 11A.

If the patient has a generalized retinal disease, such as retinitis pigmentosa, a core vitrectomy may be performed and the cells may be injected directly into a retinal blood vessel. For this purpose, a second novel needle can be used and is described below. The second novel needle can also designed to fit through a standard 23 gauge sclerotomy cannula, and angled to approximately 135 degrees at the tip portion, with the tip end tapering to approximately 42 gauge or smaller. The tip portion is sharp, angled, and stiff so that it may perforate a retinal blood vessel and allow the stem cell material, or bone marrow fraction to be injected into a retinal blood vessel.

The second novel needle (FIGS. 11A and 11B) can be made from stainless steel and can have an approximately 42 gauge or smaller polyamide tube mounted at the end of the stainless steel needle. The stainless steel portion is angled at approximately 135 to the tip and the polyamide tube is straight. The tip of the polyamide tube may be sharp to aid in perforating the retinal blood vessel. The polyamide tube may bend when inserted through the cannula into the eye. The needle is connected via tubing to a syringe containing the stem cell or bone marrow fraction material. The second novel needle may also be used to inject material under the retina.

Following injection, the second novel needle is preferably removed in the same plane as it was placed, making a self-sealing hole. Since the hole is self-sealing, no laser photocoagulation, cryopexy, gas injection or other method of sealing the hole is required. A smaller dimension needle may also be employed and various materials to manufacture the needle may be used. The needle preferably retains the stiffness and sharpness at the tip of the needle to perforate the retina while making a self-sealing hole.

If the patient has an optic nerve condition, such as ischemic optic neuropathy, a vitrectomy may be performed and the cells can be injected directly into the optic nerve. For this purpose the retinal needles described above may be used, and/or a 25 gauge 1½ inch needle may be used to directly inject the optic nerve.

It is apparent that with further advances in vitreo-retinal surgery the gauge of the cannula and the corresponding needles may decrease in size, and various materials may be used for manufacturing the needles. However, with these smaller size needles preferably the tip of the needle will still be stiff and sharp enough to perforate the retina or the retinal blood vessel while making a self-sealing incision minimizing the risk of a retinal detachment or of a hemorrhage.

Stem cell sources, other than the bone marrow, such as adipose tissue, umbilical cord blood, placental tissue, embryonic cells, including those pharmacologically manufactured, or from the systemic blood, may also be used for one or more of the above noted eye-related medical conditions.

The sizes of the eye, needles, cannulas shown in the drawings may have been enlarged as compared to their real world sizes in order to enhance their visibility for the reader.

Unless feature(s), part(s), component(s), characteristic(s) or function(s) described in the specification or shown in the drawings for a claim element, claim step or claim term specifically appear in the claim with the claim element, claim step or claim term, then the inventor does not consider such feature(s), part(s), component(s), characteristic(s) or function(s) to be included for the claim element, claim step or claim term in the claim when and if the claim element, claim step or claim term is interpreted or construed. Similarly, with respect to any "means for" elements in the claims, the inventor considers such language to require only the minimal amount of features, components, steps, or parts from the specification to achieve the function of the "means for" language and not all of the features, components, steps or parts describe in the specification that are related to the function of the "means for" language.

While the disclosure has been described and disclosed in certain terms and has disclosed certain embodiments or modifications, persons skilled in the art who have acquainted themselves with the disclosure, will appreciate that it is not necessarily limited by such terms, nor to the specific embodiments and modification disclosed herein. Thus, a wide variety of alternatives, suggested by the teachings herein, can be practiced without departing from the spirit of the disclosure, and rights to such alternatives are particularly reserved and considered within the scope of the disclosure.

What is claimed is:

1. A method for treating an eye related medical condition for a patient, comprising the following steps:
   (a) performing a bone marrow aspiration;
   (b) separating at least some of a plurality of stem cells obtained from the bone marrow aspiration;
   (c) disposing the separated stem cells within a syringe;
   (d) connecting the syringe to a subretinal needle, the subretinal needle having a first elongated member having a tip portion at an outer end and a second elongated portion that is bent to cause a first section of the second elongated portion to be positioned linear with the first elongated member and a remaining section of the second elongated portion to be positioned at an approximately 135 degrees from the first section, the tip portion of the first elongated member having a sharp outer tip end;
   (e) placing a cannula through a sclera of an eye of the patient;

(f) disposing an outer end of the subretinal needle into the cannula and ultimately within an eye area of a patient having a medical condition to be treated; and (g) administering the separated stem cells through the subretinal needle to the eye area of the patient using the syringe.

2. The method for treating of claim 1, wherein the eye related medical condition is a retinal or optic nerve condition.

3. The method for treating of claim 2 wherein for treating the retinal condition step (g) comprises administering the stem cells by a Retrobulbar Injection, a Subtenon Injection, Injection of the stem cells into the vitreous cavity with or without vitrectomy, Vitrectomy with injection of the stem cells under the retina or Vitrectomy with injection of the stem cells into a retinal blood vessel.

4. The method for treating of claim 2 wherein for treating the optic nerve condition step (g) comprises administering the stem cells by Retrolbulbar Injection, Subtenon Injection, Injection of the stem cells into the vitreous cavity with or without vitrectomy, Vitrectomy with injection of the stem cells into the optic nerve or Vitrectomy with injection of the stem cells under the retina or Vitrectomy with injection of stem cells into a retinal blood vessel.

5. The method for treating of claim 1, wherein the eye related medical condition is Age-related Macular Degeneration, Cone Dystrophy, Cone-Rod Dystrophy, Retinitis Pigmentosa (Rod-Cone Dystrophies), Stargardt's Macular Dystrophy, Myopic Degeneration, Status post Retinal Detachment repair with visual loss or Ischemic Retinopathies.

6. The method for treating of claim 1 wherein the eye related medical condition is Anterior Ischemic Optic Neuropathy, Optic Nerve Trauma, Glaucoma, Optic Atrophy, Neuromyelitis Optica, Lebers Hereditary Optic Neuropathy, Optic Nerve Hypoplasia, Autoimmune Optic Neuropathy, Dominant Optic Atrophy or Hereditary Optic Atrophy.

7. The method for treating of claim 1 further comprising the steps of placing an additional cannula into the sclera of the eye of the patient and connecting an infusion line to the additional cannula.

8. A method for treating an eye related medical condition for a patient, comprising the following steps:
(a) performing a bone marrow aspiration from a patient's iliac crest;
(b) separating at least some of a plurality of stem cells obtained from the bone marrow aspiration using a centrifuge;
(c) using the centrifuge to reduce a volume of red blood cells contained in the stem cells;
(d) disposing the separated stem cells within a syringe;
(e) connecting the syringe to a subretinal needle, the subretinal needle having a first elongated member having a tip portion at an outer end and a second elongated portion that is bent to cause a first section of the second elongated portion to be positioned linear with the first elongated member and a remaining section of the second elongated portion to be positioned at an approximately 135 degrees from the first section, the tip portion of the first elongated member having a sharp outer tip end;
(f) placing a 27 gauge or smaller gauge cannula through a sclera of an eye of the patient;
(g) disposing an outer end of the subretinal needle into the cannula and ultimately within an eye area of the patient having a medical condition to be treated; and
(h) administering the separated stem cells through the subretinal needle to the eye area of the patient using the syringe.

9. The method for treating of claim 8, wherein the eye related medical condition is a retinal or optic nerve condition.

10. The method for treating of claim 9 wherein for treating the retinal condition step (h) comprises administering the stem cells by a Retrobulbar Injection, a Subtenon Injection, Injection of the stem cells into the vitreous cavity with or without vitrectomy, Vitrectomy with injection of the stem cells under the retina or Vitrectomy with injection of the stem cells into a retinal blood vessel.

11. The method for treating of claim 9 wherein for treating the optic nerve condition step (h) comprises administering the stem cells by Retrolbulbar Injection, Subtenon Injection, Injection of the stem cells into the vitreous cavity with or without vitrectomy, Vitrectomy with injection of the stem cells into the optic nerve or Vitrectomy with injection of the stem cells under the retina or Vitrectomy with injection of stem cells into a retinal blood vessel.

12. The method for treating of claim 8 wherein the eye related medical condition is Age-related Macular Degeneration, Cone Dystrophy, Cone-Rod Dystrophy, Retinitis Pigmentosa (Rod-Cone Dystrophies), Stargardt's Macular Dystrophy, Myopic Degeneration, Status post Retinal Detachment repair with visual loss or Ischemic Retinopathies.

13. The method for treating of claim 8 wherein the eye related medical condition is Anterior Ischemic Optic Neuropathy, Optic Nerve Trauma, Glaucoma, Optic Atrophy, Neuromyelitis Optica, Lebers Hereditary Optic Neuropathy, Optic Nerve Hypoplasia, Autoimmune Optic Neuropathy, Dominant Optic Atrophy or Hereditary Optic Atrophy.

14. The method for treating of claim 8 further comprising the steps of placing an additional cannula into the sclera of the eye of the patient and connecting an infusion line to the additional cannula.

15. A method for treating an eye related medical condition for a patient, comprising the following steps:
(a) performing a bone marrow aspiration from a patient's iliac crest;
(b) separating at least some of a plurality of stem cells obtained from the bone marrow aspiration using a centrifuge;
(c) using the centrifuge to reduce a volume of red blood cells contained in the stem cells;
(d) disposing the separated stem cells within a syringe;
(e) connecting the syringe to a subretinal needle, the subretinal needle having a first elongated member having a tip portion at an outer end and a second elongated portion that is bent to cause a first section of the second elongated portion to be positioned linear with the first elongated member and a remaining section of the second elongated portion to be positioned at an approximately 135 degrees from the first section, the tip portion of the first elongated member having a sharp outer tip end;
(f) placing a 23 gauge or smaller gauge cannula through a sclera of an eye of the patient;
(g) disposing an outer end of the subretinal needle into the cannula and ultimately within an eye area of the patient having a medical condition to be treated; and
(h) administering the separated stem cells through the subretinal needle to the eye area of the patient using the syringe.

16. The method for treating of claim 15, wherein the eye related medical condition is a retinal or optic nerve condition.

17. The method for treating of claim 16 wherein for treating the retinal condition step (h) comprises administering the stem cells by a Retrobulbar Injection, a Subtenon Injection, Injection of the stem cells into the vitreous cavity with or without vitrectomy, Vitrectomy with injection of the stem cells under the retina or Vitrectomy with injection of the stem cells into a retinal blood vessel.

18. The method for treating of claim 16 wherein for treating the optic nerve condition step (h) comprises administering the stem cells by Retrolbulbar Injection, Subtenon Injection, Injection of the stem cells into the vitreous cavity with or without vitrectomy, Vitrectomy with injection of the stem cells into the optic nerve or Vitrectomy with injection of the stem cells under the retina or Vitrectomy with injection of stem cells into a retinal blood vessel.

19. The method for treating of claim 15, wherein the eye related medical condition is Age-related Macular Degeneration, Cone Dystrophy, Cone-Rod Dystrophy, Retinitis Pigmentosa (Rod-Cone Dystrophies), Stargardt's Macular Dystrophy, Myopic Degeneration, Status post Retinal Detachment repair with visual loss or Ischemic Retinopathies.

20. The method for treating of claim 15 wherein the eye related medical condition is Anterior Ischemic Optic Neuropathy, Optic Nerve Trauma, Glaucoma, Optic Atrophy, Neuromyelitis Optica, Lebers Hereditary Optic Neuropathy, Optic Nerve Hypoplasia, Autoimmune Optic Neuropathy, Dominant Optic Atrophy or Hereditary Optic Atrophy.

21. The method for treating of claim 15 further comprising the steps of placing an additional cannula into the sclera of the eye of the patient and connecting an infusion line to the additional cannula.

* * * * *